United States Patent [19]

Marrelli et al.

[11] Patent Number: 5,644,244
[45] Date of Patent: Jul. 1, 1997

[54] METHOD FOR ANALYZING A PETROLEUM STREAM

[75] Inventors: John David Marrelli, Houston; Dale Francis Brost, Sugar Land; Farhan Siddioui, Katy; Lisa Langford Pepin, Sugar Land; Joseph David Stafford, Bellaire, all of Tex.

[73] Assignee: Texaco Inc., White Plains, N.Y.

[21] Appl. No.: 374,002

[22] Filed: Jan. 18, 1995

Related U.S. Application Data

[63] Continuation-in-part of Ser. No. 718,665, Jun. 21, 1991, Pat. No. 5,383,353.

[51] Int. Cl.$^6$ .................................... G01N 22/04
[52] U.S. Cl. .................. 324/637; 324/640; 324/643; 73/61.43; 73/61.71
[58] Field of Search ..................... 324/637, 640, 324/642, 643, 698; 73/61.43, 61.71

[56] References Cited

U.S. PATENT DOCUMENTS

| | | | |
|---|---|---|---|
| 4,947,128 | 8/1990 | Hatton et al. | 324/640 |
| 4,977,377 | 12/1990 | Durrett et al. | 324/637 |
| 5,107,219 | 4/1992 | Marrelli et al. | 324/640 |
| 5,373,244 | 12/1994 | Marrelli et al. | 324/640 |
| 5,383,353 | 1/1995 | Marrelli et al. | 324/640 |
| 5,412,326 | 5/1995 | Marrelli et al. | 324/640 |

*Primary Examiner*—Kenneth A. Wieder
*Assistant Examiner*—Diep Do
*Attorney, Agent, or Firm*—Henry H. Gibson; William J. Beard

[57] ABSTRACT

Methods are provided for determining a solids to liquids ratio in a flowing petroleum stream having an immiscible solids, oil and water flow. Microwave energy in the 10–12 Gigahertz bond is directed through the petroleum stream and attenuated transmitted and reflected microwave energy are detected. The detected microwave energy is compared to an empirically derived map of attenuated amplitude vs. phase for a set of reference petroleum streams having known solid, oil and water contents to derive a solids to liquids ratio for the unknown stream.

5 Claims, 1 Drawing Sheet

METHOD FOR ANALYZING A PETROLEUM STREAM

RELATED APPLICATION

This Application is a continuation-in-part of application Ser. No. 07/718,665 filed Jun. 21, 1991 now issued as U.S. Pat. No. 5,383,353.

BACKGROUND OF THE INVENTION

FIELD OF THE INVENTION

The present invention relates to analyzers and analyzing methods in general and, more particularly, to petroleum stream analyzers and analyzing methods.

SUMMARY OF THE INVENTION

The methods of the present invention include a source of microwave energy and associated elements which provide microwave energy to a petroleum stream. Other circuitry includes elements which receive transmitted and reflected microwave energy from the petroleum stream. Electronic analyzer apparatus provides at least two outputs utilizing the provided microwave energy, the received transmitted and reflected microwave energy and known values for 100 percent oil, 100 percent solids of one species and 100 percent water, corresponding to different ratios, these ratios involving oil and water, oil and solids, water and solids, which, when mixed, are immiscible.

The objects and advantages of the present invention will appear more fully hereinafter from a consideration of the detailed description which follows, taken together with the accompanying drawings wherein one embodiment of the invention is illustrated by way of example. It is to be expressly understood, however, that the drawings are for illustration purposes only and not to be construed as defining the limits of the invention.

DESCRIPTION OF THE INVENTION

Extraction of oil from tar sands and/or diatomaceous earth, hereinafter referred to as D.E., can be accomplished by keeping the components stationary for example by pelletization of the D.E. and passing a solvent through the mixture or by flowing some combination of the mixture, water and solvent through a pipe from which desired or undesired components are extracted. However, these type of producing methods results in solids of tar sand or D.E. occurring in the produced petroleum stream. The present invention will yield the relationships water to oil, water to solids and/or solids to oil.

Figure 1:
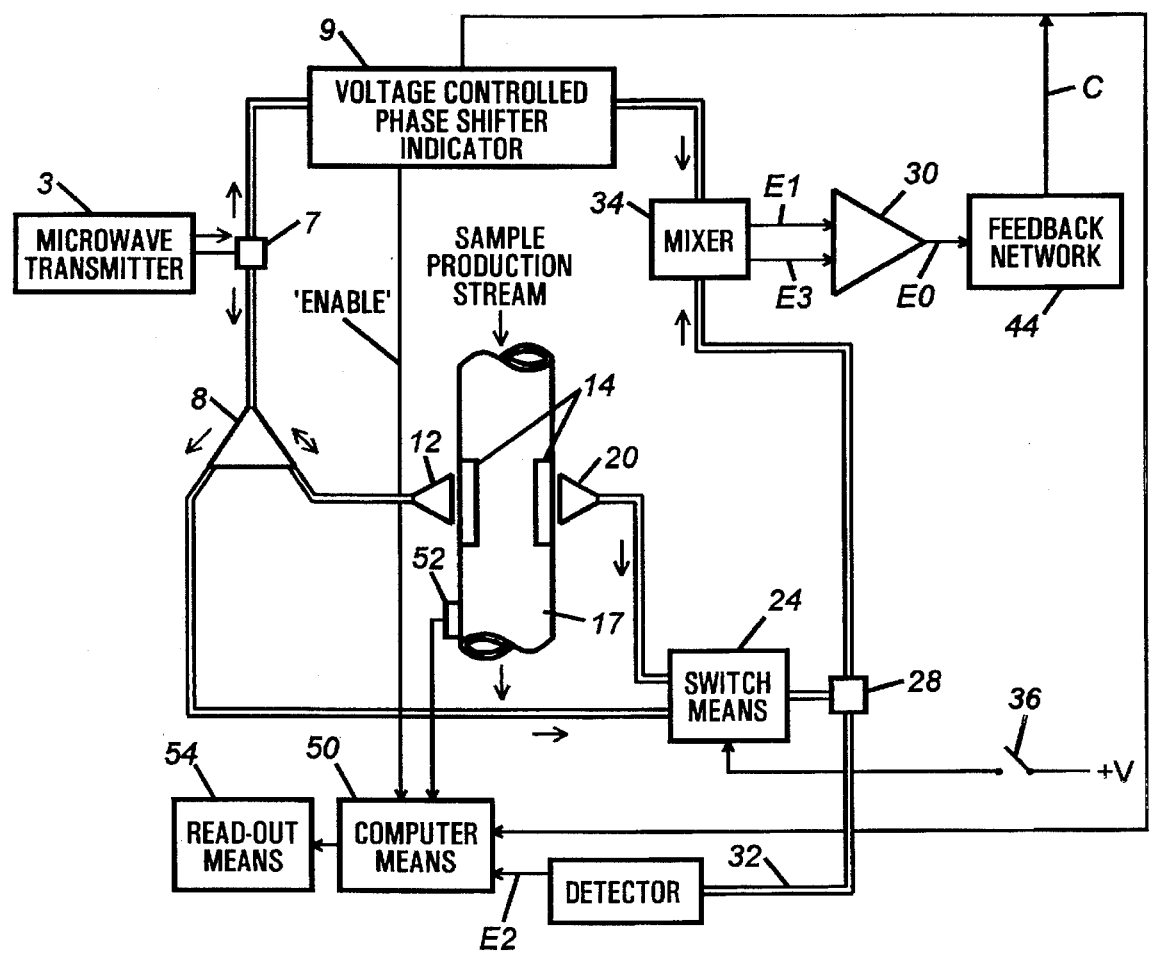
FIG. 1 is a simplified block diagram of a petroleum stream analyzer constructed in accordance with the present invention.

The analyzer shown in FIG. 1 includes a microwave source 3 providing electromagnetic energy, hereinafter referred to as microwave energy preferably in the 10–12 gigahertz band. Source 3 is low powered and may use a microwave Gunn Diode source. Source 3 provides the microwave energy to a directional coupler 7. Directional coupler 7 provides the selected microwave energy to a circulator 8 and to a conventional type voltage controlled phase shifter 9. All conductance or carrying of microwave energy is accomplished by using conventional type waveguides.

Circulator 8 provides microwave energy to an antenna 12. Antenna 12 provides the microwave energy through a window 14, which may be of a low loss dielectric material such as ceramic or teflon, to a petroleum stream having these immiscible components passing through a pipe 17. Pipe 17 may be a portion of a pipeline having windows 14 or it may be of the "window" material. The microwave energy provided by antenna 12 passes through the petroleum stream and another window 14 and is received by an antenna 20. Antenna 20 provides the received microwave energy to a switch means 24 which in turn provides the received microwave energy as test microwave energy to a directional coupler 28, as hereinafter explained. Directional coupler 28 provides the test microwave energy to a detector 32 and to a mixer 34. Detector 32 provides a signal E2 corresponding to the intensity of the microwave energy received by antenna 20.

The petroleum stream also reflects some of the microwave energy back to antenna 12 which passes back through antenna 12 to circulator 8. Circulator 8 blocks the reflected microwave energy from feeding back to source 3 and provides the reflected microwave energy to switch means 24. Reflected microwave energy becomes more important as the distance between antennas 12 and 20 increases. This is especially true where a large diameter pipeline carrying the petroleum stream is being monitored.

A positive direct current voltage +V is provided to a switch 36 which is connected to switch means 24. With switch 36 open, switch means 24 provides received attenuated microwave energy from antenna 20 as test microwave energy. When switch 36 is closed, the reflected microwave energy from antenna 12 via circulator 8 is provided by switch means 24 as the test microwave energy. In either incidence the test microwave energy is supplied to mixer 34 via a directional coupler 28.

The microwave energy from voltage controlled phase shifter 9, hereinafter called the reference microwave energy, and the test microwave energy from the directional coupler 28, are provided to mixer 34 which mixes them to provide two mixer output electrical signals E3 and E1, representative of the relative phases of the reference microwave energy and the test microwave energy, respectively. These signals are supplied to a differential amplifier 30.

The differential amplifier 30 provides an output signal EO in accordance with the difference between signals E3 and E1. Signal EO is a function of the phase difference between the reference microwave energy and the test microwave energy and is provided to a feedback network 44. Feedback network 44 provides a signal C to voltage controlled phase shifter 9, controlling the phase of the reference microwave energy, and to a mini-computer means 50. Signal EO, and hence the signal C decreases in amplitude until there is substantially 90° phase difference between the reference microwave energy and the test microwave energy. Voltage controlled phase shifter 9 indicates the amount of phase shift required to eliminate the phase difference between the test signal and the reference signal.

Signal E2 from a detector 32 which is representative of the test signal is also provided as input to computer means 50.

A temperature sensor 52 senses the temperature of the petroleum stream in pipe 17 and provides a signal T to the computer means 50 representative of the sensed temperature.

The voltage controlled phase shifter 9 also provides an enable signal to computer means 50 allowing the computer means 50 to utilize signals T, C and E2. Under some circumstances the phase difference signals can exceed 360°. Such ambiguities can be avoided and the signal "normalized" to the nearest integer multiple of 360° by monitoring the intensity of the transmitted microwave energy as described in Co-assigned U.S. Pat. No. 4,947,128.

Figure 2A:
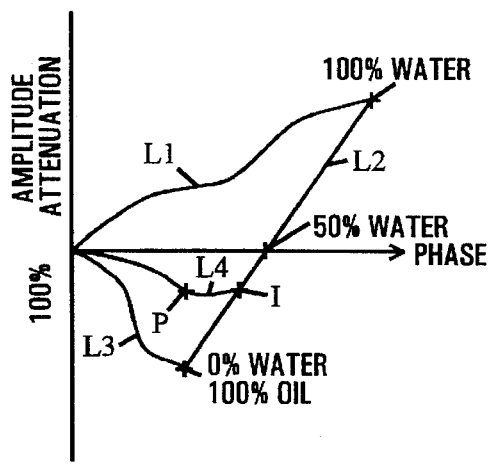
FIG. 2A is a graphical representation of a map utilized in practicing the present invention for a petroleum stream which is in a water-continuous phase.
Figure 2B:
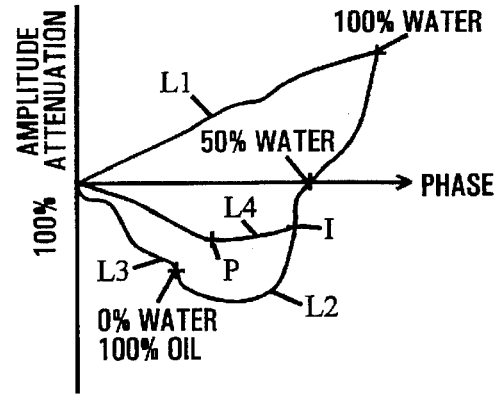
FIG. 2B is a graphical representation of a map for a petroleum stream which is in an oil-continuous phase.

FIG. 2A is a plot or "map" of a water-continuous phase petroleum stream with 100% solid D.E., 100% water and 100% oil points shown as D.E., water and oil, respectively. FIG. 2B is a "map" of an oil-continuous phase petroleum stream having solid D.E. The ordinate axes of FIG. 2A and FIG. 2B represent amplitude attenuation of the microwave energy, i.e., the amount transmitted through the petroleum stream. The abscissae axes of FIG. 2A and FIG. 2B represent the relative phase angles of a known petroleum stream having a variable solids/liquid and oil/water ratio. The maps of FIGS. 2A and 2B were developed from empirical data utilizing the following equations:

1. $Y_{L1}=f(X)$, where f(X) denotes y is a function of X, where X is equal to phase shift and y is attenuation which describes a curve L1, connecting 100% D.E. or solid to 100% water.

2. $Y_{L2}=g(X)$, where g(X) denotes y as another function of X and L2 is a curve connecting 100% oil to 100% water.

3. $Y_{L3}=H(X)$, where h(X) denotes y as yet another function of X and L3 is a curve connecting 100% D.E. or solid to 100% oil.

In all of the above described curves X is the phase angle as previously described.

In general, the maps depicted in FIGS. 2A and 2B are utilized by computer means 50 as follows. The amplitude attenuation and phase shift measurements of the microwave energies in pipe 17 for an unknown stream to be measured are shown in FIGS. 2A and 2B as point P. The procedure is the same, whether the petroleum stream is water-continuous or it is oil-continuous. A curve L4, of functional form identical to curve L3, or, as an approximation, a straight line as shown in FIG. 2A is projected by computer means 50 through the 100% D.E. solids point, through point P, to intercept curve L2, which is in essence a water-oil curve connecting the 100% water point and the 100% oil point, at point I. Point I, the intersection point of curve or line L4 and L2, yields the water cut of the petroleum stream by taking the ratio of the length along L2 from the 100% water point to the total length along L2 (from the 100% oil point to the 100% water point). Further, the D.E. or solid to liquid ratio of the stream may also be determined as the ratio of the distance from point P to point I along curve or line L4 divided by the distance from the 100% solid D.E. point to point I along curve L4. If there are no solids present in the petroleum stream, point P would lie on curve L3 and the solid to liquid ratio would be zero as the distance from point P to point I along curve L3 would be zero.

Although the foregoing has been discussed as being a water cut and a solid to liquid fraction measurement, the maps such as FIGS. 2A and 2B may also yield other ratios. Computer means 50 may generate curves such as L4 or FIG. 2B from the 100% water point to intercept curve L3. Again, that ratio of distance along such a curve to its total length would be determined in the same manner as previously discussed for the D.E. solid to liquid ratio. Computer means 50 may also generate curve such as a straight line from the 100% oil point through point P and intercept line L1. Similar ratios of distances or lengths along such a line could be interpreted as a percent of water in the petroleum stream.

We claim:

1. A method for measuring a petroleum stream having an immiscible flow of solids, water and oil comprising the steps of:

directing a beam of incident microwave energy of from 10 to 12 gigahertz frequency through the petroleum stream to be measured;

detecting attenuated microwave energy passing through the petroleum stream to be measured and using said detected reflected energy to measure the relative phase of said incident microwave energy and said attenuated microwave energy;

comparing the relative phase and amplitude attenuation of said attenuated microwave energy to an empirically derived reference map of amplitude attenuation as a function of relative phase shift for a set of reference petroleum streams having known, but varied, percentages of solids, oil and water to derive the ratio of solids to liquids in the petroleum stream to be measured.

2. The method of claim 1 wherein the comparisons are performed by determining the distance from the origin to a measured point of relative amplitude attenuation and phase shift along a generated curve of a known functional form, to the total length of said known functional form curve, from the origin to the intercept point of a generated curve connecting 100% water 100% oil points for a petroleum stream of known composition where the origin point represents 100% solids in the stream.

3. The method of claim 1 wherein said comparing step is performed by a digital computer means.

4. The method of claim 1 wherein said empirically derived map is for reference petroleum stream having oil continuous phase flow.

5. The method of claim 1 wherein said empirically derived map is for reference petroleum streams having a water continuous phase flow.

* * * * *